United States Patent [19]

Kelbaugh et al.

[11] Patent Number: 5,756,462
[45] Date of Patent: May 26, 1998

[54] PORE FORMING PEPTIDES FROM *GEOLYCOSA RIOGRANDE*

[75] Inventors: Paul R. Kelbaugh, Niantic; Robert A. Volkmann, Mystic; Nicholas A. Saccomano, Ledyard, all of Conn.

[73] Assignee: Pfizer Inc., New York, N.Y.

[21] Appl. No.: 682,621

[22] PCT Filed: Jan. 3, 1995

[86] PCT No.: PCT/IB95/00005

§ 371 Date: Jul. 18, 1996

§ 102(e) Date: Jul. 18, 1996

[87] PCT Pub. No.: WO95/19989

PCT Pub. Date: Jul. 27, 1995

Related U.S. Application Data

[63] Continuation of Ser. No. 184,097, Jan. 19, 1994, abandoned.

[51] Int. Cl.$^6$ .................. A61K 38/16; C07K 14/00

[52] U.S. Cl. .................. 514/12; 530/324; 530/858
[58] Field of Search ............. 514/12; 530/324, 530/858

[56] References Cited

U.S. PATENT DOCUMENTS 5,073,542  12/1991  Zasloff .................. 514/12

*Primary Examiner*—Cecilia J. Tsang
*Assistant Examiner*—Bennett Celsa
*Attorney, Agent, or Firm*—Peter C. Richardson; Paul H. Ginsburg; Bryan C. Zielinski

[57] ABSTRACT

Polypeptides isolated from the venom of the *Geolycosa riogrande* spider form pores in the plasma membrane of cells and are effective in mobilizing intracellular calcium ions in cells. These polypeptides are useful in such areas as drug delivery, cancer chemotherapy and immunotherapy, as well as in the physiological study of cells.

6 Claims, No Drawings

PORE FORMING PEPTIDES FROM
*GEOLYCOSA RIOGRANDE*

This application is a 371 of PCT/IB95/00003 filed Jan. 3, 1995 and a continuation of Ser. No. 08/184,097 filed Jan. 19, 1994 abandoned.

BACKGROUND OF THE INVENTION

This invention relates to polypeptides found in the venom of the *Geolycosa riogrande* spider and to polypeptides having substantially the same amino acid sequence and substantially the same activity as said polypeptides. The polypeptides and the pharmaceutically acceptable salts thereof form pores in the plasma membrane of cells and are effective in mobilizing intracellular calcium ions in cells.

Compounds which are pore formers have a variety of utilities. For example, pore forming compounds can find clinical application in drug delivery, cancer chemotherapy (e.g. immunoconjugates) and immunotherapy (e.g. immunoconjugates; complement-and cell-mediated lysis). Compounds which mobilize intracellular calcium ions have a variety of utilities, for example, in the study of the physiology of cells such as neuronal and muscle cells.

SUMMARY OF THE INVENTION

This invention concerns polypeptides found in the venom of the *Geolycosa riogrande* spider. The polypeptides of this invention and the fractions in which they are present according to this invention are as follows.

Geolycosa peptide 15a has the amino acid sequence, SEQ ID NO: 1. Geolycosa peptide 15b has the amino acid sequence, SEQ ID NO: 2. Geolycosa peptide 17 has the amino acid sequence, SEQ ID NO: 3.

The polypeptides of this invention form pores in the plasma 3 membrane of cells and mobilize intracellular $Ca^{2+}$ in cells. The main biological consequence of pore formation is cell lysis. Accordingly, therapeutants utilizing this effect may find utility in such areas as drug delivery, cancer chemotherapy (e.g. immunoconjugates) and immunotherapy (e.g. immunoconjugates; complement-and cell-mediated lysis).

Also within the scope of this invention are polypeptides which have substantially the same amino acid sequence and substantially the same pore forming and/or $Ca^{2+}$ mobilizing activity as the polypeptides described above.

This invention also concerns pharmaceutical compositions comprising said polypeptides and methods of administering said polypeptides.

DETAILED DESCRIPTION OF THE INVENTION

Venom is obtained from the *Geolycosa riogrande* spider through the process of milking by electrical stimulation according to standard methods well known to those skilled in the art. It is preferred that the method employed is one which safeguards against contamination of the whole venom by abdominal regurgitant or hemolymph, such methods are well known to those skilled in the art. The whole venom so obtained is stored in a frozen state at about −78° C. until used for purification as described below. Purification of the constituents from the whole venom is accomplished by reverse phase high performance liquid chromatography (HPLC) on a variety of preparative and semi-preparative columns such as C4 and C-18 Vydac® columns (Rainin Instrument Co. Inc., Mack Road, Woburn Mass. 01801).

Peak detection is carried out monochromatically at 220–230 nm. Further analysis of the fractions can be accomplished with, for example, polychrome UV data collected with a Waters 990 diode array detector (Millipore Corporation, Waters Chromatography Division, 34 Maple Street, Milford, Mass. 01757). The fractions from the columns are collected by known methods such as through the use of an SCO/"IFOXY" fraction collector and an ISCO 2159 peak detector (ISCO, 4700 Superior, Lincoln, Nebr. 68504). The fractions are collected in appropriately sized vessels such as sterile polyethylene laboratory ware. Concentration of the fractions is then accomplished by lyophilization from the eluant followed by lyophilization from water. Purity of the resulting constituent fractions then can be determined by chromatographic analysis using an analytical column with a gradient system which is more isocratic than the system used in the final purification of the fractions.

The polypeptides of the invention can be sequenced according to known methods. A general strategy for determining the primary structure includes, for example, the following steps. 1) Controlled cleavage of the peptide through single or multi-step enzymatic digestion/chemical cleavage. 2) Isolation and purification of peptide fragments via reverse phase high performance liquid chromatography (HPLC). 3) Characterization of peptide fragments through N-terminal sequencing and ion-spray mass spectrometry.

Given the benefit of the disclosure herein with respect to the peptides present in fractions 15a, 15b and 17 of venom from *Geolycosa riogrande*, it is now possible to obtain said peptides by methods other than through isolation/purification from whole venom. The polypeptides of this invention can be produced using recombinant DNA techniques through the cloning of a coding sequence for said polypeptides or portions thereof. For example, hybridization probes which take advantage of the now known amino acid sequence information of said polypeptides can be employed according to methods well known to those skilled in the art to clone a coding sequence for the entire polypeptide. A combination of recombinant DNA techniques and in vitro protein synthesis can also be employed to produce the polypeptides of this invention. Such in vitro protein synthesis methods include, but are not limited to, use of an ABI 430A or 433A solid phase peptide synthesizer (Applied Biosystems, Inc., 850 Lincoln Center Drive, Foster City, Calif. 94404) employing standard Merrifield chemistry or other solid phase chemistries well known to those skilled in the art.

It is well known in the art that certain amino acid substitutions can be made in polypeptides which do not affect, or do not substantially affect, the function of said polypeptides. The exact substitutions which are possible vary from polypeptide to polypeptide. Determination of permissible substitutions is accomplished according to procedures well known to those skilled in the art. Thus, all polypeptides having substantially the same amino acid sequence and substantially the same activity are within the scope of this invention.

Also within the scope of this invention are the pharmaceutically acceptable salts of the polypeptides of this invention. Such salts are formed by methods well known to those skilled in the art. For example, base salts of the polypeptides can be prepared according to conventional methods.

When a polypeptide of this invention is to be administered to a mammal, it can be administered alone or in combination with pharmaceutically acceptable carriers or diluents in a pharmaceutical composition according to standard pharmaceutical practice. The polypeptides can be administered orally or parenterally with the parenteral route of administration being preferred for polypeptides. Parenteral administration includes intravenous, intramuscular, intraperitoneal, subcutaneous and topical administration.

For oral use of a polypeptide of this invention, the compound can be administered, for example, in the form of tablets or capsules, or as an aqueous solution or suspension. In the case of tablets for oral use, carriers which are commonly used include lactose and corn starch, and lubricating agents, such as magnesium stearate, are commonly added. For oral administration in capsule form, useful diluents are lactose and dried corn starch. When aqueous suspensions are required for oral use, the active ingredient is combined with emulsifying and suspending agents. If desired, certain sweetening and/or flavoring agents can be added.

For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled to render the preparation isotonic.

When a polypeptide or salt thereof of this invention is used in a human subject, the daily dosage will normally be determined by the prescribing physician. Moreover, the dosage will vary according to the age, weight and response of the individual patient, as well as the severity of the patient's symptoms and the potency of the particular compound being administered.

When a polypeptide or salt thereof of this invention is used in the physiological study of cells, said polypeptide is administered to the cells according to methods well known to those skilled in the art. For example, said polypeptide can be administered to cells in an appropriate physiological buffer. An appropriate concentration of a polypeptide of this invention for use in such studies is 1 µM. However, the concentration of said polypeptide in such studies may be greater than or much less than 1 µM. The amount of the polypeptide administered will be determined by the person skilled in the art according to well known methods.

The two biological effects of Geolycosa peptides 15a,15b and 17 are (1) lysis of cells due to the formation of pores in the plasma membrane and (2) mobilization of intracellular $Ca^{2+}$ due to the activation of G proteins. Both these actions are shared by other small basic peptides such as mastoparan and melittin. The latter peptides are known to assume an alpha-helical structure in membranes and it is believed that this secondary structural conformation contributes greatly to the ability of these proteins to form pores and activate G proteins. The possible therapeutic significance of the Geolycosa peptides follows from these two actions.

The three peptides of the present invention isolated from the venom of the spider Geolycosa riogrande, designated Geolycosa 17, 15a and 15b, contain linear sequences of 25 (Geolycosa 17) or 27 (Geolycosa 15a and 15b) amino acids, lack cysteine, and are enriched in lysine. The ability of these peptides to mobilize intracellular $Ca^{2+}$ was evaluated in HL-60 cells differentiated with dibutryl cAMP and loaded with fura-2. When tested at concentrations of 0.5 to 2 µM, all three peptides caused rapid and transient increases in $[Ca^{2+}]_i$ that persisted in the absence of extracellular $Ca^{2+}$ but were blocked when cellular stores of $Ca^{2+}$ were depleted by pretreatment with ionomycin. Geolycosa 15a, 15b and 17 thus mobilize intracellular $Ca^{2+}$ in HL60 cells.

Small basic peptides isolated from the venom of Hymenoptera, such as mastoparan and melittin, have been shown to mobilize Intracellular $Ca^{2+}$ in various cells by an action that might involve the direct activation of a G protein(s) linked to phospholipase C. Like mastoparan and melittin, Geolycosa peptides 15a, 15b and 17 also permeabilized cells, as indexed by the uptake of ethidium bromide (EB). Uke the effect of many other pore formers, the effects of these peptides on EB uptake were augmented when the total extracellular divalent cation concentration was reduced to 0.1 mM and inhibited when extracellular $Mg^{2+}$ was increased from 1 to 5 mM. The rank order of potency for causing permeabilization of HL-60 cells was melittin>Geolycosa 15b>Geolycosa 17=Geolycosa 15a>mastoparan.

The ability of Geolycosa 17 to form pores in membranes was tested in T3 fibroblasts, parathyroid cells, and differentiated and undifferentiated HL60 cells. Pore formation was assessed by measuring the permeability of the cells to ethidium bromide (EB, MW 394). Concentrations of Geolycosa 17 greater than 7.5 µM increased EB uptake in all cells tested.

Increases in $[Ca^{2+}]_i$ arising from the mobilization of intracellular $Ca^{2+}$ were inhibited by pretreatment for 20 hrs with 100 ng/ml pertussis toxin (PTx). Prior exposure to PTx also blocked the mobilization of intracellular $Ca^{2+}$ induced by extracellular ATP.

Low concentrations of Geolycosa 17 (1–3 µM), while effective in mobilizing intracellular $Ca^{2+}$, did not cause large increases in EB uptake, even after 10 minutes.

In contrast, higher concentration of Geolycosa 17 (>10 µM) caused complete permeabilization within 5 minutes.

In all respects, Geolycosa 15a behaved similarly to Geolycosa 17. Geolycosa 15a was even less prone to cause increases in EB uptake at concentrations effective in mobilizing intracellular $Ca^{2+}$.

Geolycosa 15b behaved similarly to Geolycosa 17 and Geolycosa 15a and caused the mobilization of intracellular $Ca^{2+}$. There was little uptake of EB at concentrations found effective in mobilizing intracellular $Ca^{2+}$, although a large uptake of EB was obtained at slightly higher concentrations. Geolycosa 15b appears to be about twice as potent as Geolycosa 15a and Geolycosa 17 which are, in turn, about twice as potent as mastoparan. A major difference in the mechanism of action of Geolycosa 15b in comparison to the two other Geolycosa peptides was revealed by PTx; pretreatment with PTx failed to affect the mobilization of intracellular $Ca^{2+}$ induced by Geolycosa 15b.

Both mastoparan and melittin permeabilized HL-60 cells (and various other cell types) as assessed by EB uptake. Melittin is the most potent ($EC_{50}$ about 250 nM) in causing pore formation. Both mastoparan and melittin caused the mobilization of intracellular $Ca^{2+}$ in differentiated HL-60 cells. That induced by mastoparan was inhibited by pretreatment with PTx whereas that induced by melittin was not. Concentrations of mastoparan or melittin that mobilized intracellular $Ca^{2+}$ caused significant pore formation. Thus, in contrast to the Geolycosa peptides, there was no concentration window for these peptides that caused $Ca^{2+}$ mobilization in the absence of marked pore formation.

Geolycosa peptides behave similarly to other small basic peptides in being able to cause pore formation and the mobilization of intracellular $Ca^{2+}$. However, whereas the mobilization of intracellular $Ca^{2+}$ elicited by mastoparan or melittin is invariably accompanied by significant pore formation, that elicited by Geolycosa peptides is not. This suggests that the ability of these peptides to cause $Ca^{2+}$ mobilization is not directly related to their pore forming capacity. Indeed, while PTx blocks the effects of Geolycosa 17, Geolycosa 15a, and mastoparan on $Ca^{2+}$ mobilization, it is without effect on pore formation induced by these peptides.

EXAMPLES

Example 1

Geolycosa 17

The initial fractionation of whole venom of *Geolycosa riogrande* was carded out as follows.

Whole venom of *Geolycosa riogrande*, obtained from NPS Pharmaceuticals, Inc., Salt Lake City, Ut. 84108 and which had been stored in the frozen state at about-78° C., was thawed and 10 to 60 µl amounts thereof, diluted to 200 µl, and loaded onto a C-18 Vydac® (22 mm ×250 mm, 300 Å pore size, 10 µparticle size) column and eluted using a flow rate of 15 ml/minute and a solvent system using a linear gradient program of 80% to 60% A and 20% to 40% B over 80 minutes, where A is 0.1% aqueous trifluoroacetic acid (TFA) and B is acetonitrile. Peak detection was carded out monochromatically at 220 to 230 nm and fractions were collected with an ISCO/"FOXY" fraction collector and an ISCO 2159 peak detector. Fractions were collected from 0 to 60 minutes. Fraction 15 was collected at about 33.5 minutes and fraction 17 at 37.9 minutes.

The amino acid sequence for fraction 17 was identified as (H-)-SEQ ID NO: 3-(—$NH_2$) and was designated Geolycosa 17, mass spectrum m/z =2883.

EXAMPLES 2 and 3

Geolycosa 15a and Geolycosa 15b

Fraction 15 from Example 1, above, was subfractionated as follows.

Fraction 15, obtained as described Example 1, was loaded onto a Baker Bond Wide Pore Octadecyl (C-18, 4.6 mm×250 mm, 300 Å pore size, 5 µ particle size) column and eluted therefrom using a flow rate of 1.0 ml/minute and an isocratic solvent system of 75% A, 25% B where A is 0.1% aqueous TFA and B is acetonitrile. Peak detection was accomplished using a Waters 990 diode array detector and fraction collection was accomplished as described in Example 1. Two fractions were obtained: fraction 15a was collected at about 30 minutes and fraction 15b was collected at about 32 minutes. Fractions 15a and 15b, which comprised polypeptides, were then prepared for sequencing by lyophilization from the eluent followed by lyophilization from water, according to well known procedures.

Amino acid analysis of the alkylated polypeptide of fractions 15a and 15b were obtained using the Waters Pico-Tag method according to manufacturer's specifications. Sequence data was collected from an Applied Biosystems Model 470A Protein/Peptide sequencer (Applied Biosystems, Inc., 850 Lincoln Center Drive, Foster City, Calif. 94404) with aqueous TFA conversion. Analysis of the resulting phenylthiohydantoin amino acids was accomplished on line with an Applied Biosystems Model 120A PTH analyzer or off line on a DuPont Zorbax PTH column (Biomedical Product Department Chromatography Products, E. I. duPont de Nemours and Co., Inc., 1007 Market Street, Wilmington, Del. 19898). The amino acid sequence for fraction 15a was identified as (H—)-SEQ ID NO: 1-(—OH) and was designated Geolycosa 15a, mass spectrum m/z=3142. The amino acid sequence for fraction 15b was identified as (H—)-SEQ ID NO: 2-(—OH) and was designated Geolycosa 15b, mass spectrum m/z=3279.

---

We claim:

1. A polypeptide having the amino acid sequence:

Lys Ile Lys Trp Leu Lys Ala Met Lys Ser Ile Ala Lys Phe Ile Ala Lys Lys Gln Met Lys Lys His Leu Gly Gly Glu, or a pharmaceutically acceptable salt thereof.

2. A method of forming pores in a cell comprising administering to said cell a pore forming amount of a polypeptide according to claim 1.

3. A polypeptide having the amino acid sequence:

Lys Ile Lys Trp Phe Lys Thr Met Lys Ser Ile Ala Lys Phe Ile Ala Lys Glu Gln Met Lys Lys His Leu Lys Gly Glu, or a pharmaceutically acceptable salt thereof.

4. A method of forming pores in a cell comprising administering to said cell a pore forming amount of a polypeptide according to claim 3.

5. A polypeptide having the amino acid sequence:

Ile Trp Leu Thr Ala Leu Lys Phe Leu Gly Lys Asn Ala Ala Lys His Phe Ala Lys Arg Gln Leu Ser Lys Leu, or a pharmaceutically acceptable salt thereof.

6. A method of forming pores in a cell comprising administering to said cell a pore forming amount of a polypeptide according to claim 5.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 27 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( A ) ORGANISM: Geolycosa riogrande
        ( F ) TISSUE TYPE: venom ( x i ) SEQUENCE DESCRIPTION: SEQ ID NO:1:

```
Lys  Ile  Lys  Trp  Leu  Lys  Ala  Met  Lys  Ser  Ile  Ala  Lys  Phe  Ile  Ala
 1              5                        10                        15

Lys  Lys  Gln  Met  Lys  Lys  His  Leu  Gly  Gly  Glu
               20                       25
```

( 2 ) INFORMATION FOR SEQ ID NO:2:

```
    ( i ) SEQUENCE CHARACTERISTICS:
            ( A ) LENGTH: 27 amino acids
            ( B ) TYPE: amino acid
            ( C ) STRANDEDNESS: single
            ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
            ( A ) ORGANISM: Geolycosa riogrande
            ( F ) TISSUE TYPE: venom ( x i ) SEQUENCE DESCRIPTION: SEQ ID NO:2:

Lys  Ile  Lys  Trp  Phe  Lys  Thr  Met  Lys  Ser  Ile  Ala  Lys  Phe  Ile  Ala
     1              5                        10                        15

Lys  Glu  Gln  Met  Lys  Lys  His  Leu  Lys  Gly  Glu
                   20                        25

( 2 ) INFORMATION FOR SEQ ID NO:3:

( i ) SEQUENCE CHARACTERISTICS:
            ( A ) LENGTH: 25 amino acids
            ( B ) TYPE: amino acid
            ( C ) STRANDEDNESS: single
            ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
            ( A ) ORGANISM: Geolycosa riogrande
            ( F ) TISSUE TYPE: venom ( x i ) SEQUENCE DESCRIPTION: SEQ ID NO:3:

Ile  Trp  Leu  Thr  Ala  Leu  Lys  Phe  Leu  Gly  Lys  Asn  Ala  Ala  Lys  His
     1              5                        10                        15

Phe  Ala  Lys  Arg  Gln  Leu  Ser  Lys  Leu
                   20                        25
```